(12) United States Patent
Vogelsang et al.

(10) Patent No.: US 9,249,094 B2
(45) Date of Patent: Feb. 2, 2016

(54) METHOD FOR THE VINYLATION OF AMIDES

(75) Inventors: Regina Vogelsang, Ludwigshafen (DE); Stefan Kaeshammer, Schlifferstadt (DE); Wolfgang Staffel, Waldsee (DE); Ulrich Eiden, Kindenheim (DE); Alexandra Brand, Muehltal (DE); Lembit Tuttelberg, Mannheim (DE)

(73) Assignee: BASF SE, Ludwigshafen (DE)

( * ) Notice: Subject to any disclaimer, the term of this patent is extended or adjusted under 35 U.S.C. 154(b) by 1106 days.

(21) Appl. No.: 12/744,428

(22) PCT Filed: Dec. 8, 2008

(86) PCT No.: PCT/EP2008/067013
§ 371 (c)(1),
(2), (4) Date: May 24, 2010

(87) PCT Pub. No.: WO2009/074534
PCT Pub. Date: Jun. 18, 2009

(65) Prior Publication Data
US 2010/0249434 A1    Sep. 30, 2010

(30) Foreign Application Priority Data
Dec. 11, 2007  (EP) ..................................... 07122809

(51) Int. Cl.
*C07D 207/267*    (2006.01)

(52) U.S. Cl.
CPC ................................. *C07D 207/267* (2013.01)

(58) Field of Classification Search
CPC .................................................. C07D 206/267
See application file for complete search history.

(56) References Cited

U.S. PATENT DOCUMENTS

| 4,410,726 A | 10/1983 | Parthasarathy et al. |
| 4,873,336 A | 10/1989 | Liu et al. |
| 5,670,639 A * | 9/1997 | Schmidt-Radde et al. ... 540/485 |

FOREIGN PATENT DOCUMENTS

| DE | 32 15 093 | 1/1983 |
| DE | 195 09 362 | 9/1996 |
| EP | 0 732 324 | 9/1996 |

OTHER PUBLICATIONS

March's Advanced Organic Chemistry, 5th ed., (2001). pp. 274-305 provided.*
Dragomir et al. (Chemical Engineering Science, 60 (2005), 5049-5068).*

* cited by examiner

*Primary Examiner* — Robert Havlin
(74) *Attorney, Agent, or Firm* — Oblon, McClelland, Maier & Neustadt, L.L.P.

(57) ABSTRACT

A process for preparing an N-vinyl compound by vinylating a compound having at least one nitrogen atom (referred to hereinafter as compound for short) with acetylene, wherein
before the vinylation, the compound is reacted with an alkali metal hydroxide in a reaction zone and
the mean residence time of the alkali metal hydroxide and of the compound in the reaction zone is less than 6 minutes.

18 Claims, No Drawings

METHOD FOR THE VINYLATION OF AMIDES

The invention relates to a process for preparing an N-vinyl compound by vinylating a compound having at least one nitrogen atom (referred to hereinafter as compound for short) with acetylene, wherein, before the vinylation, the compound is reacted with an alkali metal hydroxide in a reaction zone and the mean residence time of the alkali metal hydroxide and of the compound in the reaction zone is less than 6 minutes.

A substance of particular industrial significance is N-vinylpyrrolidone, which can be prepared by vinylating pyrrolidone with acetylene. DE-A 195 09 362 discloses the reaction of pyrrolidone with an alkali metal hydroxide in a first process step and the performance of the subsequent vinylation with the reaction product of this reaction.

The reaction of pyrrolidone with an alkali metal hydroxide forms a pyrrolidate, which catalyzes the subsequent vinylation with acetylene. A disadvantage is that, in addition, by-products also form. In particular, there is opening of the five-membered ring and formation of aminobutyric acid. The by-products reduce the proportion of the pyrrolidone available for the vinylation, and hence also the overall yield of the process.

What is desired is a process in which the proportion of by-products is as low as possible. At the same time, the space-time yield should be very good; in particular, measures for reducing by-product formation should not have an adverse effect on the activity of the catalyst.

Accordingly, the process defined above has been found.

The process according to the invention is suitable for preparing any N-vinyl compounds; it is especially suitable for preparing N-vinylamides. The N-vinylamides may be cyclic (N-vinyllactams) or acyclic. Preferred N-vinyllactams are N-vinylcaprolactam, N-vinylpiperidone and N-vinylpyrrolidone. Acyclic vinylamides are especially those of the formula

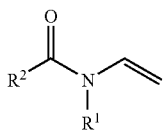

I in which R1 is a hydrogen atom or a C1 to C4 alkyl group and R2 is a C1 to C10 alkyl group.

A preferred acyclic N-vinylamide is N-vinyl-N-methylacetamide (VIMA) of the formula

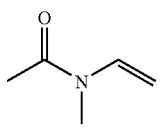

II

The starting materials for the process are compounds having at least one nitrogen atom (compound for short). In accordance with the above products, they are especially amides, whether they be cyclic amides (lactams), such as caprolactam, piperidone or pyrrolidone, or acyclic amides, such as acetamide or N-methylacetamide.

In a particularly preferred embodiment, the compound is pyrrolidone and the N-vinyl compound obtained therefrom is N-vinylpyrrolidone.

In a further preferred embodiment, the compound is N-methylacetamide and the N-vinyl compound is N-vinyl-N-methylacetamide (VIMA).

According to the invention, the compound is first reacted with an alkali metal hydroxide. This may, for example, be lithium hydroxide, sodium hydroxide or potassium hydroxide; particular preference is given to potassium hydroxide. In addition to pure alkali metal hydroxide, it is also possible to use commercially available alkali metal hydroxide, especially KOH, with small amounts of impurities, for example a content of chlorides and/or carbonates.

The alkali metal hydroxide is preferably used in the form of an aqueous solution. The content of alkali metal hydroxide may, for example, be from 5 to 90% by weight, based on the solution; in particular, it is from 30 to 60% by weight, more preferably from 45 to 55% by weight.

The reaction of the compound with the alkali metal hydroxide is effected preferably at temperatures of from 50 to 250° C. and from 1 mbar to 1 bar, especially at from 20 to 250° C. The temperature at the top of the column is preferably from 20 to 100° C., especially from 25 to 60° C.; the temperature in the bottom of the column is preferably from 100 to 250° C., especially from 120 to 200° C.

The process is preferably conducted semicontinuously or continuously. Particular preference is given to conducting it continuously.

Preference is given to effecting the reaction in a column, more preferably in a column with random packing or structured packing, which is operated at the aforementioned temperatures and pressures. It is preferably operated continuously.

Also suitable are columns which comprise both random packings and structured packings, for example comprise beds of random packings in the lower section and have packing elements (for example installed steel sheets) in the upper section.

The column has preferably at least two, more preferably at least 3 theoretical plates. It may have, for example, from 2 to 100, especially from 3 to 20 theoretical plates.

The alkali metal hydroxide and the compound are preferably added to the column in the upper third, more preferably in the upper quarter, of the column.

The mean residence time of the alkali metal hydroxide and of the compound in the reaction zone, i.e. column, is less than 6 minutes, especially less than 5 minutes; more preferably, it is from 50 to 200 seconds.

The reaction forms the corresponding alkali metal salt of the compound, for example, in the case of pyrrolidone, the pyrrolidate, i.e. potassium pyrrolidate.

The amount of alkali metal hydroxide is preferably selected such that from 0.25 to 25% by weight, preferably from 1 to 10% by weight, of the compound is present in the form of the alkali metal salt (pyrrolidone as the pyrrolidate, i.e. potassium pyrrolidate).

The product of the reaction can be drawn off continuously in the lower part of the column or at the bottom of the column. Subsequently, the compound is then reacted with acetylene, preferably in a separate reaction vessel.

The alkali metal salt catalyzes the subsequent reaction with acetylene (vinylation). The effluent from the above column can be mixed with further compound (pyrrolidone). The compound used for the vinylation (pyrrolidone) may then comprise especially from 0.25 to 10% by weight, especially from 1.5 to 6% by weight, of pyrrolidate.

By virtue of the process according to the invention, it is possible to obtain N-vinyl compounds, for example N-vinylpyrrolidone, in high yield and purity. In particular, the proportion of by-products, for example, in the case of N-vinylpyrrolidone, that of the aminobutyric acid by-product and of the by-products which arise through reaction of aminobutyric acid with acetylene, is significantly reduced.

The resulting N-vinyl compound, especially the N-vinylpyrrolidone, can, if appropriate, be removed by distillation and can generally be obtained with a purity of more than 99% by weight, more preferably of more than 99.5% by weight. The space-time yield of the overall process, including the subsequent vinylation, is still very good. The short residence time in the reaction of the compound with the alkali metal hydroxide accordingly does not have an adverse effect on the catalytic activity.

EXAMPLES

Example 1

2-Pyrrolidone and 50% KOH solution in water were initially charged, and the water and water which formed were distilled off under reduced pressure within one hour (residence time). In the reaction mixture thus prepared, aminobutyric acid and oligomers and hydrolysis products were found in significant amounts.

Example 2

2-Pyrrolidone and a 48% by weight KOH solution in water were introduced into the liquid distributor of a column with random packing, and the water from the KOH and the water which formed were removed in this column. The residence time in the reaction zone was less than 100 seconds.

Aminobutyric acid and conversion products thereof could not be detected in the reaction product.

The invention claimed is:

1. A process for preparing an N-vinyl compound, comprising vinylating a compound having at least one nitrogen atom with acetylene, wherein
before the vinylation, the compound is reacted with an alkali metal hydroxide in a reaction zone and
a mean residence time of the alkali metal hydroxide and of the compound in the reaction zone is less than 5 minutes.

2. The process according to claim 1, wherein the N-vinyl compound is an N-vinylamide.

3. The process according to claim 1, wherein the N-vinyl compound is N-vinyl-N-methylacetamide or N-vinylpyrrolidone.

4. The process according to claim 1, wherein the alkali metal hydroxide is potassium hydroxide.

5. The process according to claim 1, wherein the alkali metal hydroxide is in the form of an aqueous solution.

6. The process according to claim 1, wherein the reaction is effected in a column comprising the reaction zone.

7. The process according to claim 6, wherein the column has random packing and has at least 2 theoretical plates.

8. The process according to claim 6, wherein the alkali metal hydroxide and the compound are added in an upper third of the column.

9. The process according to claim 6, wherein the column is operated at a pressure of from 1 mbar to 1 bar and a temperature of from 20 to 250° C.

10. The process according to claim 1, wherein the mean residence time of the alkali metal hydroxide and of the compound in the reaction zone is from 50 to 200 seconds.

11. The process according to claim 1, wherein the vinylation of the compound is effected in a subsequent process.

12. The process according to claim 1, wherein, said alkali metal hydroxide is in the form of an aqueous solution having an alkali metal hydroxide content of from 5 to 90% by weight.

13. The process according to claim 1, wherein, said alkali metal hydroxide is in the form of an aqueous solution having an alkali metal hydroxide content of from 30 to 60% by weight.

14. The process according to claim 1, wherein, said alkali metal hydroxide is in the form of an aqueous solution having an alkali metal hydroxide content of from 45 to 55% by weight.

15. The process according to claim 6, wherein said column has from 2 to 100 theoretical plates.

16. The process according to claim 6, wherein said column has from 3 to 20 theoretical plates.

17. The process according to claim 1, wherein an amount of alkali metal hydroxide is such that from 0.25 to 25% by weight of said compound is present in the form of an alkali metal salt.

18. The process according to claim 1, wherein an amount of alkali metal hydroxide is such that from 1 to 10% by weight of said compound is present in the form of an alkali metal salt.

* * * * *